United States Patent [19]

Carbonari

[11] Patent Number: 5,271,899
[45] Date of Patent: Dec. 21, 1993

[54] CHEMISTRY ANALYZER

[75] Inventor: Larry A. Carbonari, Toms River, N.J.

[73] Assignee: Bio-Chem Laboratory Systems, Inc., Lakewood, N.J.

[21] Appl. No.: 916,210

[22] Filed: Jul. 17, 1992

[51] Int. Cl.[5] .......................................... G01N 35/00
[52] U.S. Cl. .......................................... 422/67; 422/63; 422/64; 422/99; 422/100; 436/43; 436/50; 436/55; 436/49; 436/180
[58] Field of Search ..................... 422/67, 63, 64, 65, 422/99, 100; 436/43, 48, 49, 54, 174, 180, 50, 55

[56] References Cited

U.S. PATENT DOCUMENTS

| | | | |
|---|---|---|---|
| 3,951,608 | 4/1976 | Trod | 422/64 |
| 4,147,752 | 4/1979 | Suovaniemi et al. | 422/57 |
| 4,681,742 | 7/1987 | Johnson et al. | 422/102 |
| 4,767,600 | 8/1988 | Vicario | 422/65 |
| 4,803,050 | 2/1989 | Mack | 422/65 |
| 5,084,240 | 1/1992 | Babson | 422/72 |
| 5,120,503 | 6/1992 | Hinckley et al. | 422/102 |
| 5,183,638 | 2/1993 | Wakatake | 422/64 |
| 5,185,269 | 2/1993 | Wells | 436/180 |

*Primary Examiner*—James C. Housel
*Assistant Examiner*—Long V. Le
*Attorney, Agent, or Firm*—John N. Bain; William Squire

[57] ABSTRACT

A generally spherical bead on the floor of a compartment is prevented from lying in the path of insertion of an elongated member into the compartment when the compartment is located at a site. A drive mechanism first moves the compartment relatively slowly and a small distance away from the site so that the inertia of the bead causes it to move with the compartment away from the insertion path. The compartment is then moved relatively quickly back to the site so that the inertia of the bead prevents it from moving with the compartment, to thereby position and maintain the bead away from the insertion path. The compartment has a relatively planar floor integral with side walls. When the compartment is at the site, a first side wall is adjacent to the insertion path and a second opposed side wall is remote from the insertion path. The bead is rollable between the opposed side walls on the floor along the general line of movement of the compartment, the bead initially occupying and remaining in one of its numerous possible positions on the floor when the compartment is first moved slowly. The floor of the compartment moves under the bead until the second side wall contacts it and its inertia holds it thereagainst when the compartment is then moved quickly.

9 Claims, 2 Drawing Sheets

CHEMISTRY ANALYZER

The present invention relates to an improved chemistry analyzer and more particularly to improved apparatus for automatically conducting immunological, immunoassay testing on a general analyzer.

BACKGROUND OF THE INVENTION

A wide variety of automatic and semi-automatic chemistry analyzers are known and are commercially available. These analyzers mimic and automate a variety of test procedures and methodologies which were previously performed manually. A typical chemistry analysis, whether performed automatically, semi-automatically or manually, involves a variety of samples to be tested and analyzed, as well as a varity of diluents and reagents to be used.

A typical biochemical analysis involves the addition of a sample to a reaction vessel, following which a reagent is added thereto. The mixture is stirred and a second or additional reagents may be thereafter added, all followed by stirring. After sufficient time for a desired reaction to take place has occurred, the liquids in the reaction vessels are analyzed by fluorescent, radioactive or colorimetric techniques.

In conducting an immunological analysis, such as an enzyme-immono-assay ("EIA") analysis, a measured amount of a sample, which may contain a measured amount of a diluent, is added to a reaction vessel. The vessels also hold a carrier, such as a glass or synthetic resin bead, which has an antibody or antigen fixed on the surface thereof. A first or conjugate reagent is then added the ultimate effect of which is to bind the selected antibody or antigen to the bead. After removing the first reagent and washing or rinsing, following passage of a selected time, next added to the reaction vessel are second and third reagents. Following the passage of another selected time, during which a desired reaction takes place, which separates the bound and the free antibodies or antigens and to otherwise react with substances bound to the bead to produce a test liquid, which is ultimately withdrawn or decanted from the test vessel and colorimetrically analyzed by a photometer. The foregoing description applies generally to all EIA tests, including heterogeneous EIA tests of both the competitive and the sandwich types.

If semi-automatic or automatic apparatus is provided to conduct the above testing steps, then washing and rinsing of reaction vessels, in addition to that required directly for purposes of the test, is clearly required for a subsequent test to be conducted on different samples.

Typical automatic chemistry analyzers include a plurality of reaction vessels, a plurality of containers for samples, and a plurality of containers holding various reagents and water. In a typical prior art chemistry analyzer, the various liquid samples and reagents are removed from the sample containers and the reagent containers and are placed into and removed from the reaction vessels by a facility which comprises a robotic arm or head.

The robotic arm is mounted for rotational movement about a vertical axis and is also capable of rotating about a horizontal axis so that the head may be moved vertically up and down. The arm typically carries one or more hollow tubes, or hypodermic needle-like members, and flexible tubing connecting the tubes or members to appropriate pumps. The robotic arm and the pumps are used to remove a sample from a sample container, to place the removed sample into a reaction vessel, to remove a selected first reagent from a reagent container, and to then place the reagent into the reaction vessel holding the sample. In order to avoid contamination, for example of the reagent by the sample, the tubes may be first immersed in a "home" position well, which contains rinsing water, after the sample has been placed in the reaction vessel but before removal of the reagent. The rinsing water is removed from the passes through and rinses the needless and the tubing and is transported to a waste liquid container at a remote location.

After the appropriate reaction has taken place in the reaction vessel, the robotic arm is operated so as to remove the first reagent from the reaction vessel, rinse the vessel and the head, place the second and third reagents in the vessel—rinsing the second reagent from the needle before placing the third reagent—and transporting the contents of the vessel for testing by a photometer or the like, to which the liquid is conducted by the tubing and the pumps. If an EIA test is being performed, the above general description of the prior art apparatus is a bit more lengthy and complicated because the glass bead in the reaction vessel is rinsed and washed several times before fluid is decanted from the reaction vessel for transmission to the photometer.

In most prior art automatic chemistry analyzers, the various vessels and containers are carried in a moveable carrier, typically a circular carrier. Movement of the robotic arm, and the various movable carriers, is appropriately coordinated under the control of a programmed microprocessor to automatically effect a plurality of tests on various samples. In one preferred arrangement, the reaction vessels comprise compartments formed in a quarter-circular member called a sector. Four sectors are carried by a circular turntable, which is selectively operated by a stepping motor under the control of the microprocessor. The sectors are positioned at the periphery of the turntable. Also carried by the turntable, and closer to the center thereof, are sample containers. When the turntable is at a selected position, the robotic arm may be operated so that its needle may be inserted into a selected reaction vessel and/or a selected sample container for placement or removal of liquid thereinto. Thus, the needle of the robotic arm can reach all of the reaction vessels and all of the sample containers, but can do so only in conjunction with rotation of the turntable or carrier to appropriately position each thereof. The reagent containers are contained on the circumference of a circle, the center of which defines the vertical rotation axis of the robotic arm. Thus, the carrier for the reagent containers may be stationary since the needle-like member of the robotic arm can access each of the reagent containers.

Some difficulty has been experienced in making a chemical analyzer of the type described above compact and in adapting such an analyzer in convenient fashion to perform both general and EIA tests. Specifically, as previously noted, EIA tests involve the use of solid-phase bead technology. When these tests are automated, they involve the insertion of the robotic arm's needle-like member into the reaction vessels both to deposit and to remove liquids therein. Because of the extent of the insertion of the needle-like member necessary to ensure that liquid in the vessel is removed, it has been found that the presence of the bead in the container can interfere with and/or block the operation of the needle-like member in placing or withdrawing liquids. One solution to this problem would be to make the reaction vessel sufficiently large or deep so that the presence of the bead would cause no interference with the needle-like member of the robotic arm. However, following this course is counter to the trend of making automatic chemical analyzers as compact and low profile as possible. One solution to the foregoing problem is described in U.S. Pat. No. 4,837,159, which involves the use of specially shaped reaction vessels which add to the cost and complexity of the equipment.

Prior art manual techniques, particularly as they relate to EIA tests, involve not only multiple rinsing steps but also involve the need to stir, shake, mix or agitate a mixture of liquids at various times. The prior art provides for a variety of means for stirring or agitating liquids involved in chemical analyses, but these tend to involve rather complicated mechanical structures in addition to the other structures required for automatic analysis. For various stirring or agitating apparatus, see the following U.S. Pat. Nos. 4,774,055; 4,383,041; 4,981,801; 4,200,607; 5,104,807. There is a need for a simple, yet effective, method of stirring, mixing or agitating fluids in the reaction vessels which does not add significantly to the size, cost and complexity of the automatic apparatus.

The prior art also recognizes the need to control the temperatures of the various liquids involved in chemistry analyzing. In the automatic or semi-automatic apparatus of the prior art, temperature control is effected typically by maintaining the environment in the vicinity of one or more of the liquid containers involved at a given temperature so that reactions using such liquids are carried out at or near such known temperature. See, for example, U.S. Pat. No. 4,981,801 and 4,200,607. It is felt to be desirable to provide improved apparatus for more accurately maintaining the temperature of the various liquids involved in chemical analysis by automatic and semi-automatic equipment.

A primary object of the present invention is the provision of an improved chemistry analyzer of the type described above, which eliminates some of the disadvantages of prior art apparatus, and achieves the aforenoted goals related to needle interference by the beads involved in EIA analyses, agitation or stirring of liquid mixtures in conducting chemical analyses, and temperature control.

SUMMARY OF THE INVENTION

With the above and other objects in view, the present invention relates primarily to an improved automated chemistry analyzer that incorporates solid phase bead technology. In one broad aspect, the present invention relates to apparatus which insures that a bead used in a reaction vessel during the conducting of an EIA analysis, does not lie on the path of insertion of a tube, needle or similar elongated member into the compartment when the compartment is located at a particular site. The needle is so inserted into the reaction vessel for purposes of placing into or removing therefrom liquid. The presence of the bead on the path of needle insertion can, in prior devices, interfere with the function of the needle.

Facilities are provided for first moving the reaction vessel relatively slowly and a small distance away from the site so that the inertia of the bead causes it to move with the vessel away from the insertion path. Following the foregoing, the facilities then move the vessel relatively quickly back to the site so that the inertia of the bead prevents it from moving with the vessel. This positions the bead and maintains it away from the insertion path.

Preferably, the reaction vessel has a relatively planar floor integral with sidewalls. A first sidewall of the reaction vessel is adjacent to the insertion path and a second opposed sidewall is remote from the insertion path when the reaction vessel is at the site. The bead may roll between the opposed sidewalls on the floor along the general direction of movement of the reaction vessel. The bead occupies, and remains in, one of its numerous possible positions on the floor between the opposed sidewalls when the compartment is first moved slowly. The floor of the compartment moves under and relative to the bead until the second sidewall contacts it and its inertia holds it against the second sidewall when the compartment is moved quickly. The floor may be contoured to encourage the bead to assume a position away from the first sidewall and to encourage the bead to remain in the position adjacent to the second sidewall until the needle descends into the reaction vessel. Specifically, the liquids are less dense than the bead, and frictional, wetting and other forces among the liquids, the bead and the floor inhibit or prevent the bead's movement along the floor toward the second wall, absent the movement of the compartment first away from and then back into the site.

The reaction vessel may be one of numerous reaction vessels carried by a moveable carrier. Each reaction vessel is individually positionable at the site. Facilities such as a stepping motor may move the carrier to selectively present the reaction vessels at the site. Preferably, the carrier-moving facilities and the vessel moving facilities are the same, that is, they constitute a single stepping motor or funtionally equivalent motive source. In this event, facilities, such as a programmed processor, are provided which selectively operate the moving facility to first locate a selected reaction vessel at the site and to then move the located vessel away from and back to the site to position the bead therein away from the insertion path of the needle.

In the second aspect, the present invention relates to improved apparatus, such as an improved chemistry analyzer, for depositing and mixing together various liquids in a vessel such as a reaction vessel. The apparatus also includes a container for a first liquid and a container for a second liquid. A tube or needle facility is also provided for separately removing the first liquid from its container prior to the addition of the second and third liquids without contaiminating one reagent with another container and for depositing the liquids in the vessel. Also provided are facilities for inserting the tube or needle facility into the vessel during or after placement of the liquids therein and for thereafter rapidly vibrating the tube facility to mix the liquids together. Facilities are also provided for moving the tube facility among the containers and the vessel prior to insertion of the tube facility thereinto for liquid removal or placement.

Preferably, the tube or needle facility includes a hollow needle-like member and a selectively operable pumping system which is connected to the needle for selectively withdrawing liquids from the containers and the vessel and for selectively placing the withdrawn liquids into the vessel. Vibration of the tube facility vibrates the needle to mix the fluids.

In specific embodiments, such as where the foregoing apparatus is present in a chemistry analyzer, a plurality of containers each holds a different first liquid and a plurality of containers each holds a different second and third liquid stationary. A plurality of reaction vessels may be carried and stopped by a moveable carrier. Facilities are also provided for moving the reaction vessel carrier relative to a deposit site for insertion into a selected vessel of the member to effect deposit of the first and second liquids thereinto and the mixing of the deposited liquids. In preferred embodiments, the reaction vessel may carry beads therewithin, where an EIA test is being conducted. In this event, the apparatus also includes facilities for ensuring that the beads do not lie in the path of insertion of the member into the vessels when the vessels are located at the deposit site. As with the present invention in its first aspect, this facility may be as previously described.

In a third aspect, the present invention relates to maintaining the various liquids used in chemistry analyses at desired temperatures so that reactions may proceed at known rates and to known degrees. In this aspect of the present invention, a needle is moved to remove liquids from various containers to hold the removed liquids and to deposit the liquids in reaction vessels. Selected containers for the held liquids are temperature controlled as required by the reactions to be carried out to assure constant and timely reaction.

DETAILED DESCRIPTION

Figure 1:
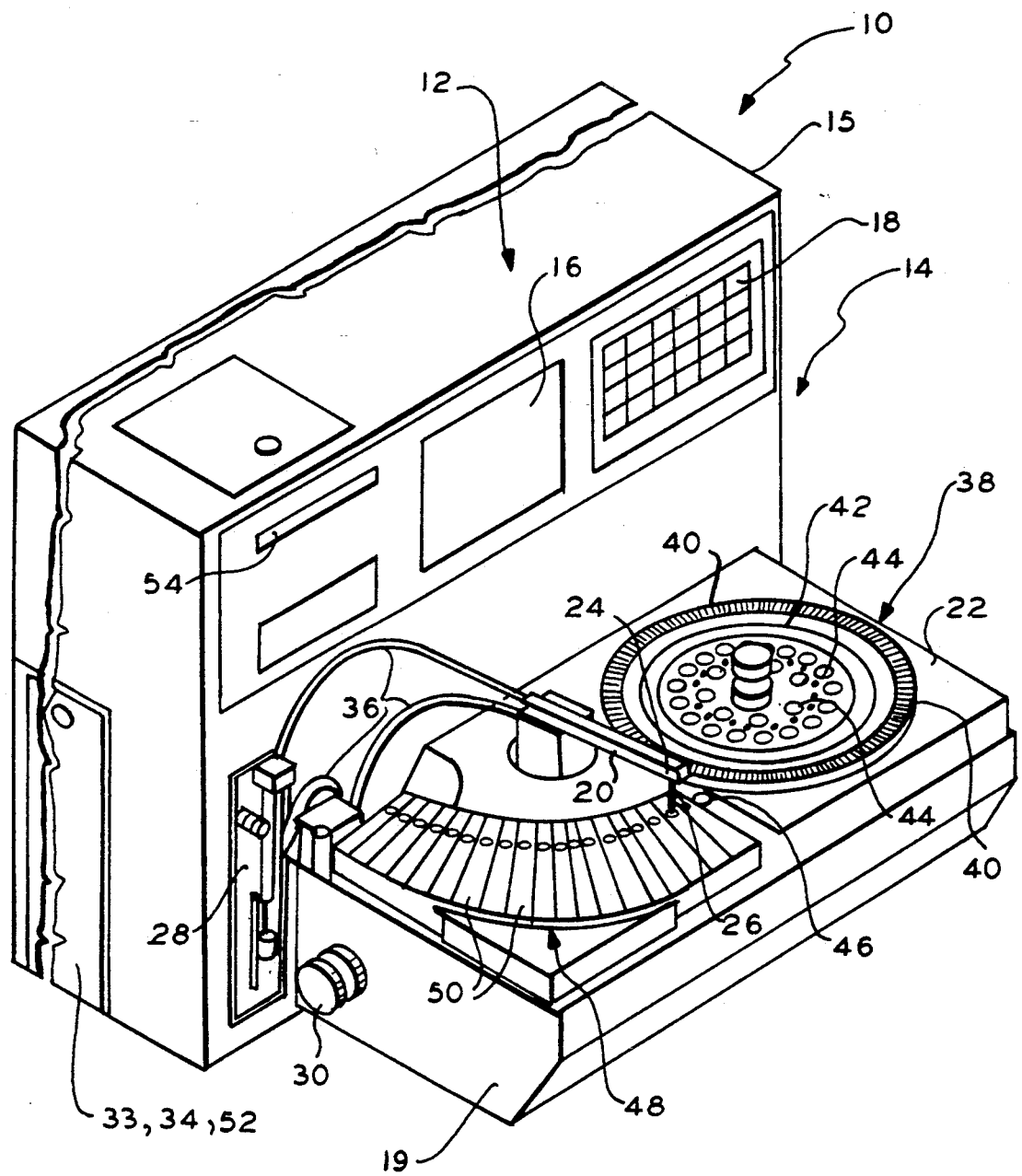
FIG. 1 is a front elevation of a chemistry analyzer which includes the various aspects of the present invention.

Referring first to FIG. 1, a chemistry analyzer 10 for the automatic performances of general chemistry tests and EIA tests on specific body fluids, such as blood serum, blood plasma and urine generally includes a control section 12 and an electromechanical work station 14. The control section 12, which is mainly contained and hidden within a cabinet 15, may include a variety of microprocessors (not shown), other chips and similar devices, such as RAM's (not shown), power supplies (not shown), and other associated electrical components (not shown). As set forth in the above-identified prior art patents and elsewhere in the prior art, the specifics of the control section 12 are not important to the present invention as long as the function of the various elements described below is performable or controlable thereby.

The visible portion of the control section 12 includes a CRT display 16 and a touch pad 18. The display 16 permits the user to examine various menus listing a variety of tests and displays a variety of test-related information such as the results thereof. The touch pad 18 permits the user to direct the control section 12 to operate the unit 10 to perform selected tests on selected samples. In preferred arrangements, the operation and function of the various elements of the unit 10 may be controlled and affected by a program stored in a microprocessor and/or a RAM. The stored operation may be altered or otherwise affected, as well as sequenced, by appropriate operation of the touch pad 18. The tests which the unit 10 is programmed to perform may be displayed on the CRT display 16, which may also display the status of a test while it is being conducted, as well as the results at its conclusion. Those skilled in the art will know that latitude is possible, as well as known, regarding the operation of the control section 12, the CRT display 16 and the touch pad 18.

The work station 14 includes a variety of items, some of which are only generally shown. These items are carried by, or are otherwise fixed to, a base 19 which may be integral with, or otherwise attached to, the cabinet 15.

A robotic arm 20 is pivotally mounted to a platform 22, which is carried by the base 19. The robotic arm 20, which is preferably of a type known to the art, is mounted at one end to the platform 22 for rotary motion about a vertical axis. The arm 20 may also be rotated about a horizontal axis to move its free end or head 24 in an up-and-down manner. The head 24 may also rotate about a generally horizontal axis coincident with the arm 20. Movement of the arm 20 and of its head 24 is effected by one or more stepping motors (not shown), which are controlled by one or more of the processors, chips, RAMs or the like in the control section 12. As is well known, these stepping motors are located in the base 19 and are connected to the arm 20 via appropriate transmissions and connections.

The head 24 carries one or more thin, hollow members 26, which preferably comprise hypodermic needle-like members. The needles 26 are connected by flexible tubing 36, also carried by the arm 20, to various other portions of the unit 10, as described below. Fluids may be directed in either direction through the needles 26 by pumps 28 and 30 connected to the tubing 36. Motors (not shown), which operate these pumps 28 and 30, are also controlled and operated by the control section 12. The needles 26, the pumps 28 and 30, a water reservoir 32, and a waste reservoir 34, the latter two being hidden within the unit 10 by the cabinet 15, are appropriately interconnected by the tubing 36. Preferably, the pump 28 may be a calibrated piston-cylinder-type of syringe pump, while the pump 30 may be a systolic pump, although clearly, other pumps may be used if desired. The calibrated piston-cylinder pump 28 permits measured, metered amounts of liquid to be drawn into the needles 26 or to be expelled from the needles 26, while the systolic pump 30 permits high-quantity, high-speed pumping of fluids when such is necessary. Either pump may be operated in such a fashion so as to move liquid through the needles 26 and the tubing 36 in either direction and to "hold," multiple different liquids. That is to say, so-called air bubble separation may be effected in which one liquid is drawn into one of the needles 26 or its associated tubing 36 followed by subsequent drawing in of air and then another liquid whereupon the air or air bubble between the two masses of fluid separates the two fluids which may thus be separately held, transported and dispensed or otherwise moved to a desired location. The "timing" of this operation is under the control of the control section 12.

A carrier, such as a selectively rotatable turntable 38, is mounted in a recess in the platform 22 and is carried by the base 19. The turntable 38 is selectively rotatable by a stepping motor (not shown) controlled by the control unit 12. The turntable 38 holds a plurality of sectors 40, each of which define or contain a plurality of reaction vessels 42. In the depicted embodiment, each sector 40 subtends an angle of about 90°. The four sectors 40 rotate with the turntable 38. The reaction vessels 42 are open at the top so that liquids may be placed therein and removed therefrom by the needles 26.

Figure 3:
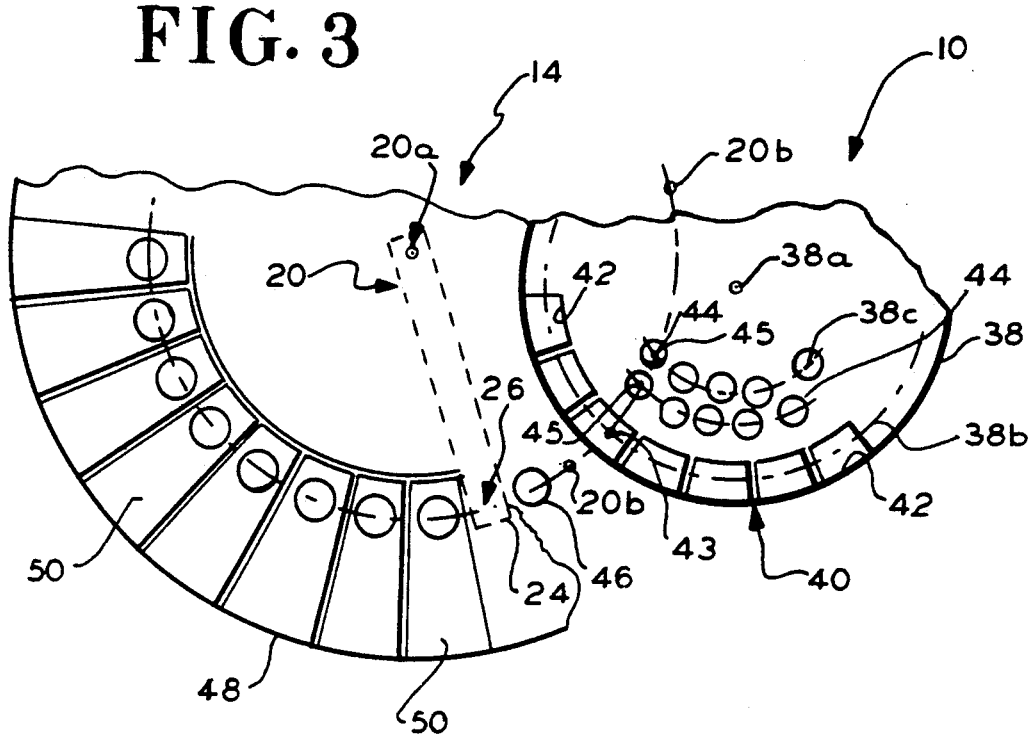
FIG. 3 is a schematic top view of the invention shown in FIGS. 1 and 2.

As shown in FIG. 3, the arm 20 rotates about a vertical axis 20a to move its head 24 along a circumference 20b. The turntable 38 rotates about a vertical axis 38a to move the reaction vessels 42 about its circumference 38b. The circumferences 20b and 38b intersect at a site 43, which is defined herein as a placement/removal site 43. Specifically, when a reaction vessel 42 is located at the site 43, the needles 26 on the head 24 may be inserted into the vessel 42. Such insertion of the needles 26 permits liquids to be placed in the vessel 42 through the needles 26 or liquid to be withdrawn from the reaction vessels 42 by the needles 26. As noted above, the rotation of the turntable 38 is selectively effected by the control section 12 operating a stepping motor. Thus, when it is desired to place liquids in a given reaction vessel 42, or to remove liquids from such vessel 42, the turntable 38 is appropriately rotated to locate the selected reaction vessel 42 at the site 43, and the arm 20 is rotated to position the needles 26 over the open top of the vessel 42. The arm 20 is thereafter rotated to lower the head 24 and the needles 26, thereby inserting the needles 26 into the vessel 42.

In preferred embodiments of the present invention, the turntable 38 also holds a plurality of containers 44, which may be tubes or open-ended cylinders. These containers 44 are intended to contain various body fluids or samples which are to be analyzed by the unit 10. As shown, more than one circular array of these containers 44 may be present. The containers 44 are rotatable with the turntable 38 as are the reaction vessels 42.

Referring again to FIG. 3, as with the reaction vessels 42, the containers 44 are moved along a circular path 38c and about the vertical axis 38a of the turntable 38. This circular path 38c is also intersected by the circumference 20b at a removal site 45. Thus, to remove a body fluid sample from a container 44, the turntable 38 is rotated to present the selected container 44 at the removal site 45. Thereafter, the arm 20 is rotated to position its head 24 over the container 44 whereupon the needles 26 are inserted into the container 44 to remove a selected amount of the sample. Thereafter, the needles 26 are withdrawn from the container 44, the arm 20 is rotated to position the needles 26 over a selected reaction vessel 42 (rotation of the turntable 38 will typically be necessary to position the selected reaction vessel 42 at the site 43), and the needles are inserted into the reaction vessel 42 at the site 43, whereupon the liquid is placed therein.

The unit 10 may also include a permanent, or "home," tube 46 mounted in the platform 22. This tube 46 may be constantly supplied with fresh, de-ionized water or other selected liquid for purposes of rinsing and washing the needles 26 and the tubes 36. Obviously, the tube 46 lies on the circumference 20b and may be conveniently located as desired.

The platform 22 also carries a tray 48. The tray 48 may carry a number of individual containers 50 which hold a variety of reagents, diluents, or the like. The containers 50 may be open-topped or may, as shown, have access openings thereinto, which lie on the circumference 20b.

As so far described, the unit 10 may be operated in a selected fashion to place in the reaction vessels 42 liquid samples from the containers 44 and reagents and diluents from the containers 50 for purposes of permitting selected reactions to take place within the vessels 42. Appropriate rinsing and washing stops may be effected when needed. Following the occurrence of the reactions, the control section 12 may effect operation of the arm 20 to withdraw from the reaction vessels 42 at the site 43 the reaction products or liquids containing these reaction products, which may then be transported to an analytical device via the tubing 36.

A general chemistry test is performed as follows. Selected containers 44 holding various sample fluids are placed in the turntable 38 at appropriate positions. The tray 48 is loaded with containers 50 having appropriate reagents or diluents for such tests. The robotic arm 20 is next moved and operated so as to insert the needles 26 into the appropriate containers 44 and to remove therefrom quantities of the liquids upon operation of the pumps 28 and 30. The robotic arm 20 is then moved and operated to insert the needles 26 into selected reaction vessels 42 whereat the body fluids are deposited. In performing these aforenoted functions, the control section 12 operates the various stepping motors for the turntable 38, the arm 20 and the pumps 28 and 30 to achieve the desired results. Thereafter, the robotic arm 20 is further operated and moved so that the needles 26 and the pumps 28 and 30 remove a measured quantities of reagents and diluents from the containers 50 and place these reagents in selected reation vessels 42. After appropriate rection times have elapsed, as determined by the control section 12, the control section 12 causes operation of the robotic arm 20 to permit the needles 26 to remove measured quantities of the contents of the reaction vessels 42 which are now transmitted via the tubing 36 by the action of the pumps 28 and 30 to a photometric or other analyzer 52 within the unit 10. The results of the photometric tests are processed within the control section 12 and are ultimately displayed on the display 16 and on a paper tape by a paper tape printer 54. Of course, the results may also be transmitted via modem, telecommunication port or the like to a remote receiving station, which may include a PC, a printer or other terminal.

General chemistry tests may involve the addition of more than one reagent or diluent. In that event, the control unit 12 simply operates the robotic arm 20 in the desired fashion, to place in the reaction vessels 42 all of the liquids necessary for the appropriate test. As already noted, if it is desired to rinse the needles 26 or the tubing 36 between the various liquid-withdrawal and liquid-placement steps, the needles 26 may be periodically inserted into the tube 46 for rinsing and washing of the needles 26 and the tubing 36. Although the aforedescribed unit 10 involves the carrying of the reaction vessels 42 and the sample containers 44 on a common turntable 38, these could clearly be carried on different turntables if desired. Of course, this would probably involve an increase in size or "footprint" of the unit 10. Similarly, the reagent and diluent containers 50 as shown are carried in a stationary tray 48. This tray 48 could be differently located or could be mounted on a turntable. Various placements of trays, turntables and the like is well within the skill of the art, as shown by the prior art patents cited above.

Solid phase EIA tests are generally similar to general chemistry tests, but have not in the past been typically performed on a unit similar to the unit 10. There are several reasons for this. In a solid phase EIA test, each reaction between body fluids or portions thereof and reagents occur with a small bead immersed therein. The bead holds on its surface various reaction products or reagent-modified substances following the occurrence of all of the desired reactions. Typically, in solid phase EIA testing, a series of different reactions and rinsing are serially carried out in the presence of one bead. Between each reaction, there occur multiple rinsing steps of the reaction vessel 42 to remove from the vessel 42 all residue of a first or conjugate reagent except that which is bound to the surface of the bead 60. Ultimately, after second and third reagents have been added, and all such reactions have taken place, the bead resides in a body of liquid, a portion of which is then drawn off and subjected to a photometric test reading. As is well-known, and as can be seen from the immediately foregoing description, EIA testing, whether manual or automatic, involves repetitive pippetting and multiple rinsing steps. Moreover, in many chemistry tests but particularly in EIA testing, it has been found necessary to periodically mix the various liquid mixtures which exist in the reaction vessels 42 at various times. Failure to so mix these liquids can result in inaccurate test results. It is the repetitiveness of these numerous steps which makes EIA testing by automatic apparatus as disclosed herein attractive.

Figure 2:
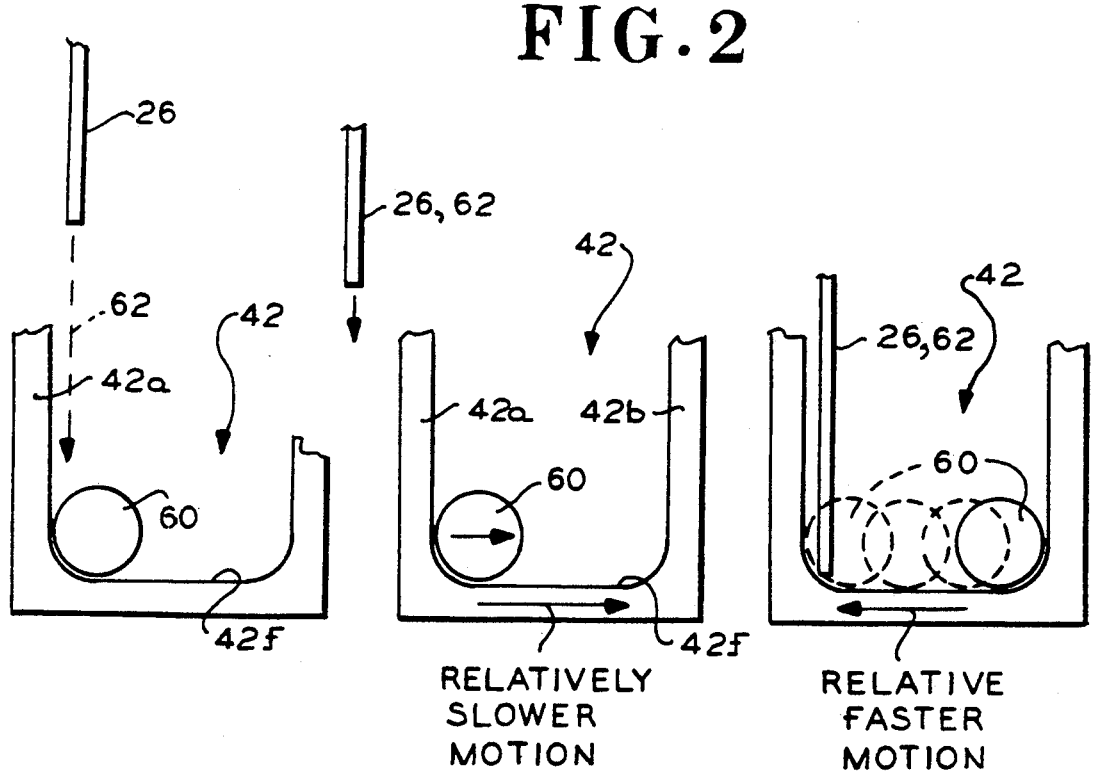
FIG. 2 illustrates in detail one of the aspects of the present invention which relates to the use of solid phase beads for EIA teseting.

As diagrammatically depicted in FIG. 2, a bead 60 present in a reaction vessel 42 during the conduction of an EIA test, is somewhat smaller than the dimension of the reaction vessel 42 in the direction of movement of the turntable 38. As is well known, the bead 60 may be made of a plastic resin or other suitable material. Early attempts by the present inventor to automatic an EIA test along the lines of the unit 10 described above led to the recognition that the bead 60 could interfere with the insertion of and the operation of the needle 26 into the reaction vessel 42. The presence of the bead 60 on the path of insertion 62 of the needle 26 could interfere with the liquid placement or liquid withdrawal function of the needle 26 or might damage the needle 26. Liquid withdrawal may require the tip of the needle 26 to reach the floor 42f of the reaction bessel 42 to effect removal of substantial all liquid therein. The U-shaped reaction tubes of U.S. Pat. No. 4,837,159 reflect one approach to ensuring that the beads 60 do not interfere with the placement or withdrawal of liquid. However, as noted earlier, this solution is deemed to be overly complex and expensive.

Early attempts to keep the bead 60 away from the path of insertion 62 of the needle 26 was to slope or indent the floor 42f of the reaction vessel 42. However, it was found that frictional wetting, electrostatic short order and or other forces did not permit the beads 60 to reliably roll down the slanted floor away from the insertion path 62. Indeed, it was determined that beads 60 in the reaction vessels 42 tended to occupy random positions some of which could cause the needles 26 to function improperly. Accordingly, there was devised the "inertial positioning" technique of the present invention as viewed in FIG. 2. Specifically, when EIA tests are being conducted and beads 60 are present in the reaction vessels 42, as or just before the needles 26 are lowered into a selected reaction vessel 42, the stepping motor for the turntable 38 is operated in impulse-like fashion to rotate the turntable 38 relatively slowly away from the site 43. The distance of this rotation is short and following it the turntable 38 is "jerked" or rotated relatively quickly to move the reaction vessel 42 back to the site 43. The rotation in the first direction moves the bead 60 with the turntable and the floor 42f of its reaction vessel 42 in that direction. When the turntable 38 rotates quickly in impulse fashion back to position the reaction vessel 42 at the site 43, the inertia of the bead 60 permits the floor 42f to move relatively thereto—in effect, the bead 60 remains stationary, or nearly so—until the bead 60 engages the forward wall 42b of the reaction vessel 42. The site 43 is intentionally chosen so that the path of insertion 62 of the needle 26 is adjacent or near a rearward wall 42a of the reaction vessel 42 and away or remote from the forward wall 42b of the reaction vessel 42. Thus, this inertial positioning of the bead 60 maintains it away from the insertion path 62 of the needle 26.

The timing of this inertial positioning is crucial. Inertial positioning of the bead 60 away from the insertion path 62 is timed so that the needles 26 do not strike the walls of the vessel 42 or impinge on the bead 60. In a time-efficient automatic unit 10 inertial positioning of the bead 60 is best effected to occur in a timed fashion as the needle 26 is being lowered for insertion into the reaction vessel 42 by the arm 20.

The occurrence of inertial positioning is of course under the control of the control section 12. Inertial positioning has been found to be extremely effective in successfully automating solid phase EIA testing on the unit 10.

As noted above, some chemistry tests and particularly EIA testing, also involve the necessity of periodically mixing the various liquids in the reaction vessel 42. The various prior art patents as noted above, show a variety of means for achieving stirring or agitation, all of which are to some extent complicated and add to the cost and size of the automatic units in which they are contained. In the present invention, the head 24 of the arm 20 may be rotated about a horizontal axis as noted. To this end and under the control of the control section 12, the appropriate stepping motor associated with the arm 20 is operated to rapidly vibrate or oscillate the needles 26 back and forth. This rapid oscillation occurs when the needles 26 have been inserted into the fluid held in a reaction vessel 42.

In conducting EIA tests, it has been found beneficial to mix the liquids and the bead 60 in the reaction vessels 42 periodically. Mixing every 60 seconds or so is sufficient to ensure that the proper reactions take place in a timely fashion. To this end, the control section 12 periodically operates the stepping motor for the turntable 38 to move the reaction vessels 42 back and forth a short distance for several cycles. The stepping motor is energized so that, given the fictional force between the floor 42f of the vessel 42 and the bead 60, the bead rolls in the vessel 42 in aid of the mixing. The foregoing operation ensures that the liquids in the vessel 42 experience total and homogenous mixing and that there is good contact between the mixed liquids and the bead 60.

Many tests, both general chemistry and EIA, are temperature sensitive. To stabilize the temperature of liquids under test, a variety of heating and cooling facilities have been used in the prior art as shown by the above-noted prior art patents. The present unit 10 utilizes two heaters (not shown) to stabilize the temperature of liquids involved in testing. One heater 70 is located in the robotic arm so that fluids passing through the needles 26 and the tubing 36 and which are held therein after its removal from a container 44 and 50 until placed in a reaction vessel 42, are maintained at the appropriate temperature. The other heater 72 is located below the platform 22 in proximity to the turntable 38 so that the liquids in the containers 44 are maintained at a known temperature.

While the foregoing describes preferred embodiments of the present invention as those having skill in the art will appreciate at various changes and modifications can be made thereto without departing from the spirit and scope of the following claims.

I claim:

1. In an apparatus including a bead on a floor of a compartment, an elongated member insertable into the compartment along an insertion path when the compartment is located at a site, wherein the improvement comprising:

control means for controlling movements of said compartment; and means responsive to the control means for ensuring the bead does not lie on said insertion path of said elongated member, said means for ensuring comprising (a) first moving the compartment at a first rate a distance away from the site so that the inertia of the bead during said moving causes the bead to move with the compartment away from the insertion path and (b) for then moving the compartment back to the site at a second rate greater than the first rate so that the inertia of the bead during said moving back at said second rate prevents the bead from moving with the compartment, to thereby position and maintain the bead away from the insertion path.

2. Apparatus as in claim 1, wherein:

the compartment has a planar floor integral with side walls, when the compartment is at the site, a first side wall being adjacent the insertion path and a second opposed side wall being remote from the insertion path, the bead being rollable between the opposed side walls on the floor along a line of movement of the compartment, the bead initially occupying and remaining in a position on the floor when the compartment is first moved at said first rate, the floor of the compartment moving under the bead until the second side wall contacts the bead and the bead's inertia holds the bead thereagainst when the compartment is moved at said second rate.

3. Apparatus as in claim 2, wherein:

the compartment holds liquids less dense than the bead; and frictional and wetting forces between the liquids and the bead inhibiting the bead's movement along the floor toward the second wall absent the movement of the compartment first at said first rate away from and then at said second rate back to the site.

4. Apparatus as in claim 2, which further comprises:

means for placing liquids into and for removing the liquids from the compartment through the elongated member when the compartment is at the site and the elongated member is inserted into the compartment along the insertion path.

5. Apparatus as in claim 4, wherein:

the liquids are less dense than the bead which remains on the floor, frictional and wetting forces among the bead, the liquid and the floor inhibiting the bead's movement along the floor toward the second wall.

6. Apparatus as in claim 5, wherein:

the movement of the compartment away from and back to the site is effected in impulse fashion.

7. Apparatus as in claim 6, which further comprises:

a movable carrier having plural vessels including said compartments and which are positionable at the site; and means for moving the carrier to selectively present the compartments at the site.

8. Apparatus as in claim 7, wherein the carrier-moving means further comprises means selectively to first locate selected vessels at the site and then move the located vessels away from and back to the site to position the beads thereon away from the insertion path.

9. In a device including at least one reaction vessel movable to and away from a site for holding liquids a tube facility insertable along an insertion path into a vessel at the site for placing liquids in or withdrawing liquids from the vessel, and a bead in the vessel, the improvement comprising:

control means for controlling movements of said reaction vessel; and means responsive to the control means for ensuring that the bead does not lie on the insertion path of and, accordingly, does not interfere with insertion of the tube facility thereinto, said means for ensuring comprising:

(a) means for moving the vessel a distance away from the site at a first rate, the inertia of the bead causing it to move with the vessel away from the insertion path, and (b) means for moving the vessel at a second rate greater than the first rate back to the site, the second rate being sufficiently great so that the inertia of the bead is such that the bead remains away from the insertion path.

* * * * *